United States Patent
Corbett et al.

(10) Patent No.: US 8,702,942 B2
(45) Date of Patent: Apr. 22, 2014

(54) LASER DOPPLER ELECTROPHORESIS USING A DIFFUSION BARRIER

(75) Inventors: Jason Cecil William Corbett, Hereford (GB); Malcolm Connah, Malvern (GB); Kevin Mattison, Sterling, MA (US)

(73) Assignee: Malvern Instruments, Ltd., Malvern (GB)

( * ) Notice: Subject to any disclaimer, the term of this patent is extended or adjusted under 35 U.S.C. 154(b) by 314 days.

(21) Appl. No.: 12/972,412

(22) Filed: Dec. 17, 2010

(65) Prior Publication Data
US 2012/0152745 A1    Jun. 21, 2012

(51) Int. Cl.
G01N 27/447 (2006.01)
G01N 27/453 (2006.01)
G01N 27/26 (2006.01)
G01N 15/02 (2006.01)
G01N 21/00 (2006.01)

(52) U.S. Cl.
USPC ........... 204/457; 204/600; 204/643; 204/450; 204/547; 356/344; 356/337; 356/450; 356/28.5; 435/287.1; 422/68.1; 422/82.01

(58) Field of Classification Search
USPC .................. 204/547, 600–643, 450, 457; 435/287.1, 287.2, 6.19; 422/68.1, 422/82.01; 356/344, 337, 450, 28.5
See application file for complete search history.

(56) References Cited

U.S. PATENT DOCUMENTS

| | | | | |
|---|---|---|---|---|
| 3,870,612 A | * | 3/1975 | Flygare et al. | 204/549 |
| 4,101,220 A | * | 7/1978 | Bean et al. | 204/549 |
| 4,242,194 A | * | 12/1980 | Steiner et al. | 204/645 |
| 6,406,602 B1 | | 6/2002 | Cahill | |
| 2002/0040851 A1 | * | 4/2002 | Mc.Neil-Watson et al. | 204/549 |
| 2011/0210002 A1 | * | 9/2011 | Hsieh et al. | 204/549 |

FOREIGN PATENT DOCUMENTS

| | | | |
|---|---|---|---|
| GB | 1194112 | * | 2/1988 |
| GB | 2368904 A | | 5/2002 |
| GB | 2399879 A | | 9/2004 |

OTHER PUBLICATIONS

Corbett et al. (Electrophoresis 2011, 32, 1787-1794).*
Uzgiris (Rev.Sci.Instrum., vol. 45, No. 1, 1974).*
Zetasizer Nano Series User Manual, Issue 2.1, Jul. 2004.*
Uzgiris, Progress in Surface Science, vol. 10, 53-164, 1981.*
Goff, "Measurement of colloid mobility by laser doppler electrophoresis: the effect of salt concentration on particle mobility", Journal of Colloid and Interface Science, Jun. 1, 1984, pp. 468-483, vol. 99, No. 2, Academic Press, New York, NY, US.
Mohan, "Laser Doppler spectroscopy as applied to electrophoresis in protein solutions", Analytical Biochemistry, Feb. 1, 1976, pp. 506-525, vol. 70, No. 2, New York, NY, US.

* cited by examiner

*Primary Examiner* — Jennifer Dieterle
(74) *Attorney, Agent, or Firm* — Kristofer E. Elbing

(57) ABSTRACT

In one general aspect, an electrophoretic measurement method is disclosed that includes providing a vessel that holds a dispersant, providing a first electrode immersed in the dispersant, and providing a second electrode immersed in the dispersant. A sample is placed at a location within the dispersant between the first and second electrodes with the sample being separated from the electrodes, an alternating electric field is applied across the electrodes, and the sample is illuminated with temporally coherent light. A frequency shift is detected in light from the step of illuminating that has interacted with the sample during the step of applying an alternating electric field, and a property of the sample is derived based on results of the step of detecting.

13 Claims, 7 Drawing Sheets

LASER DOPPLER ELECTROPHORESIS USING A DIFFUSION BARRIER

FIELD OF THE INVENTION

This invention relates to methods and apparatus for performing electrophoretic measurements, including laser Doppler electrophoresis measurements that use diffusion barriers.

BACKGROUND OF THE INVENTION

There are a number of techniques that have been used to measure the electrophoretic mobility of soft samples such as capillary zone electrophoresis, membrane confined steady state electrophoresis, the Tiselius apparatus, and electrophoretic light scattering, including Laser Doppler Electrophoresis (LDE). LDE measures mobility of particles by measuring particle motion under the application of an external electric field. Referring to FIG. 1, the particles 16 are dispersed in a buffer 14 and electrodes 24, 26 are immersed into the sample. The field is applied and at very high buffer conductivities and degradation of the sample can occur at the electrode surface. For protein samples it is also believed that the oxidation-reduction reaction at the electrode surface ionizes bonds within the protein structure creating aggregates 18 which then both adhere to the electrode surface and are dispersed into the rest of the sample. The volumes typically associated with LDE can also be problematic due to high sample cost and the iterative nature of LDE measurement optimization.

SUMMARY OF THE INVENTION

In one general aspect, the invention features an electrophoretic measurement method that includes providing a vessel that holds a dispersant, providing a first electrode immersed in the dispersant, and providing a second electrode immersed in the dispersant. A sample is placed at a location within the dispersant between the first and second electrodes with the sample being separated from the electrodes, an alternating electric field is applied across the electrodes, and the sample is illuminated with temporally coherent light. A frequency shift is detected in light from the step of illuminating that has interacted with the sample during the step of applying an alternating electric field, and a property of the sample is derived based on results of the step of detecting.

In preferred embodiments the step of placing the sample can include injecting the sample. The step of placing the sample can be part of a process of drawing the sample through the vessel. The method can further include a step of recovering the sample. The sample can be a soft sample. The sample can be a protein sample. The step of placing the sample can place the sample at a location separated from the electrodes by dispersant. The step of placing the sample can place the sample at a location separated from the electrodes by a barrier different from the dispersant. The step of deriving can include deriving a zeta potential value from an electrophoretic mobility value for the sample. The step of detecting can take place in a time that is shorter than a time during which a significant amount of the sample can diffuse to either of the first and second electrodes with the alternating current applied. The step of illuminating can employ a laser.

In another general aspect, the invention features an electrophoretic instrument that includes a vessel, a first electrode, a second electrode. A first diffusion barrier is located between the sample location and the first electrode, and a second diffusion barrier is located between the sample location and the second electrode. A temporally coherent illumination source is positioned to illuminate the sample location, and a frequency-shift detector is positioned to receive illumination from the sample location after interaction with the sample.

In preferred embodiments, the instrument can further include a sample introduction channel to introduce a sample at a sample location in the vessel. The sample introduction channel can include a needle. The sample introduction channel can include a port. The instrument can further include including a sample extraction channel to extract the sample at the sample location in the vessel. The first diffusion barrier can include a volume of dispersant and the second diffusion barrier includes a volume of dispersant. The first and second diffusion barriers can include a conductive gel. The vessel can be a generally upright u-shaped vessel. The u-shaped vessel can further include a sample introduction port having an opening proximate openings of the u-shaped vessel. The u-shaped vessel can further include a sample extraction port having an opening proximate openings of the u-shaped vessel. The u-shaped vessel can further include sample introduction and extraction ports each having an opening proximate openings of the u-shaped vessel. The vessel can be a disposable plastic vessel. The illumination source can be a laser. The instrument can further include a zeta potential derivation unit to derive a zeta potential value from an electrophoretic mobility value measured by the detector for the sample.

Generally, this document describes a diffusion barrier concept, whereby a small volume of the sample itself (dispersed or otherwise) is introduced into a larger volume, that includes the electrodes, prefilled with dispersant only. The diffusion barrier is intended to isolate the sample from the electrode surface whilst maintaining electrical contact with the surface, via the buffer within which the sample is dispersed. The LDE measurement ideally occurs before the sample has migrated to the electrode or if an extended measurement duration is required then before the aggregates created at the electrodes have migrated back into the light scattering detection volume. The sample volumes are also, by default, then greatly reduced and since, ideally, the sample is not degraded at the electrode then significantly more measurements are available in order to properly optimize the measurement. It may also then be possible to retrieve the sample after the measurement, depending on the physical format of the sample cell. Whilst primarily aimed at protein or other soft samples, the technique can also be used to increase cell life by the reduction of blackening of the electrodes.

There are a number of preferred embodiments, including a three port cuvette, a four port cuvette, and unique ways of filling a currently offered folded capillary cell (FCC). These cells can all be implemented as cells for a standard cuvette holder such as is found in the Zetasizer Nano (Malvern Instruments Ltd, Malvern, UK).

Systems according to the invention can be advantageous in that they can help to avoid the creation of aggregates in electrophoretic mobility measurements on protein samples. This can potentially reduce a source of errors in these measurements, because the aggregates can have very different mobilities from those of the native protein itself. And although some researchers have shown that the blackening of the electrodes does not affect the quality of the measurement, this blackening is extremely unsightly and the perception in the marketplace is that it indicates a 'dirty' and therefore unusable cell.

DETAILED DESCRIPTION OF AN ILLUSTRATIVE EMBODIMENT

Figure 1:
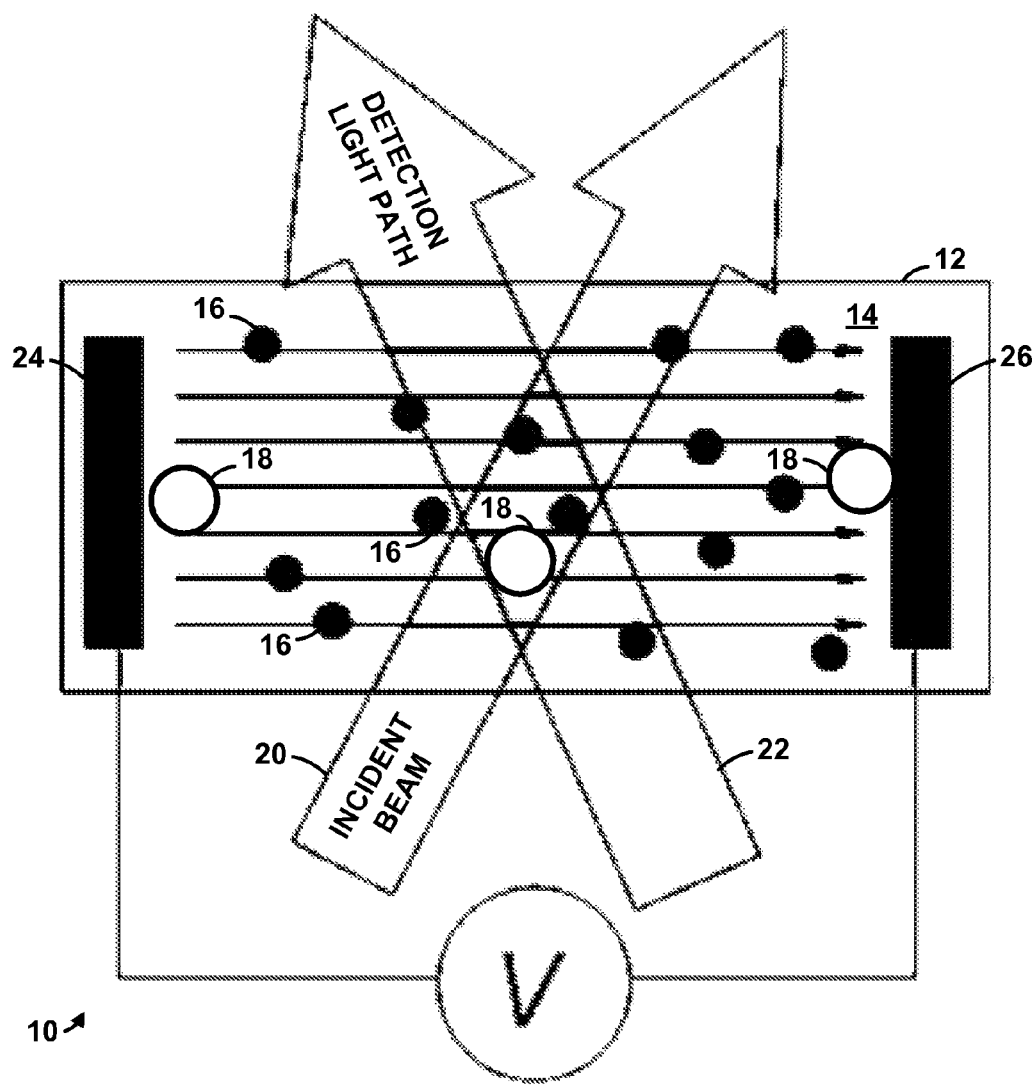
FIG. 1 is a schematic diagram illustrating a prior art electrophoretic measurement.
Figure 2A:
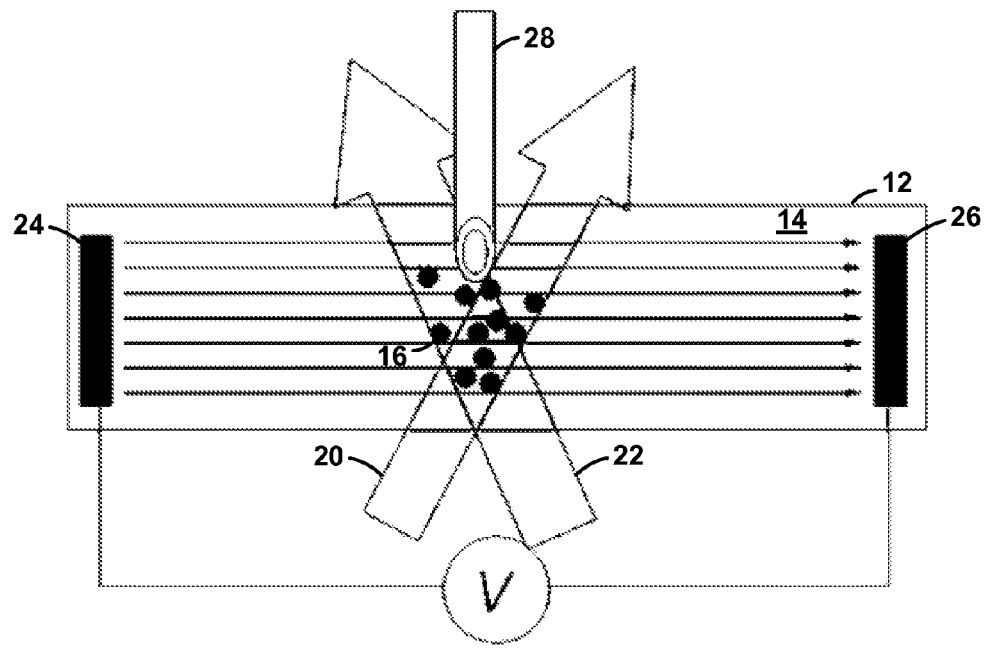
FIG. 2A is a schematic diagram illustrating an electrophoretic apparatus according to the invention at the beginning of an electrophoretic measurement.
Figure 2B:
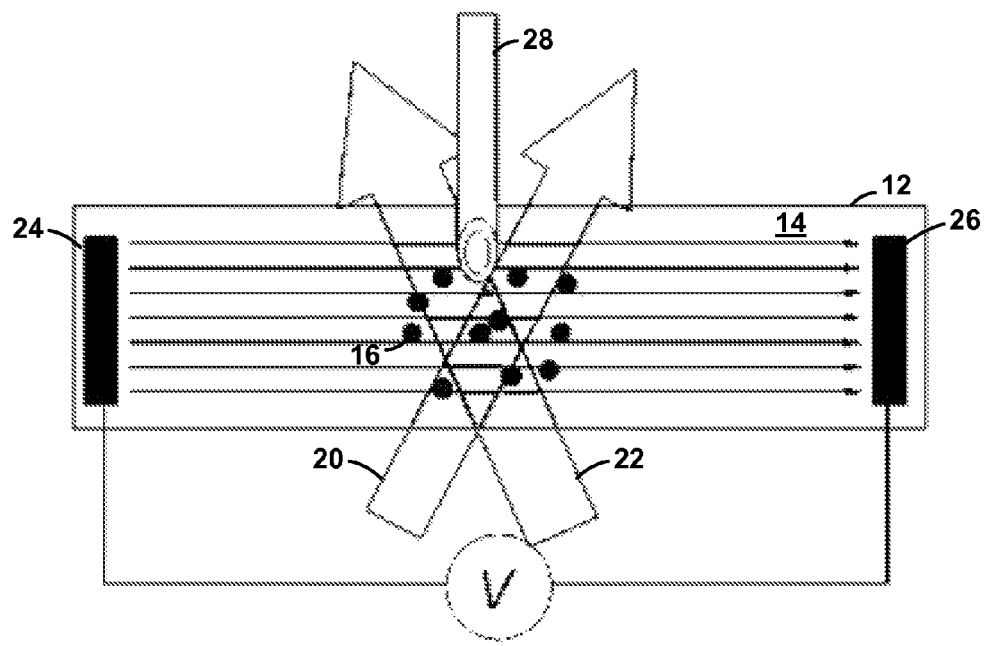
FIG. 2B is a schematic diagram illustrating the electrophoretic apparatus shown in FIG. 2A after a first time period has elapsed during the electrophoretic measurement.
Figure 2C:
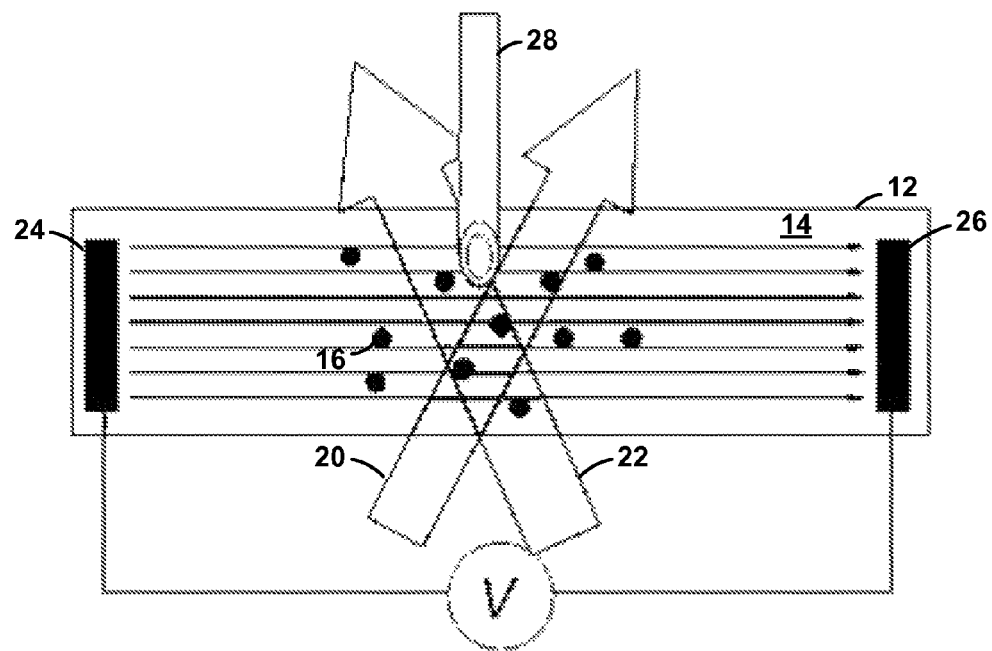
FIG. 2C is a schematic diagram illustrating the electrophoretic apparatus shown in FIG. 2A after a second time period has elapsed during the electrophoretic measurement.
Figure 2D:
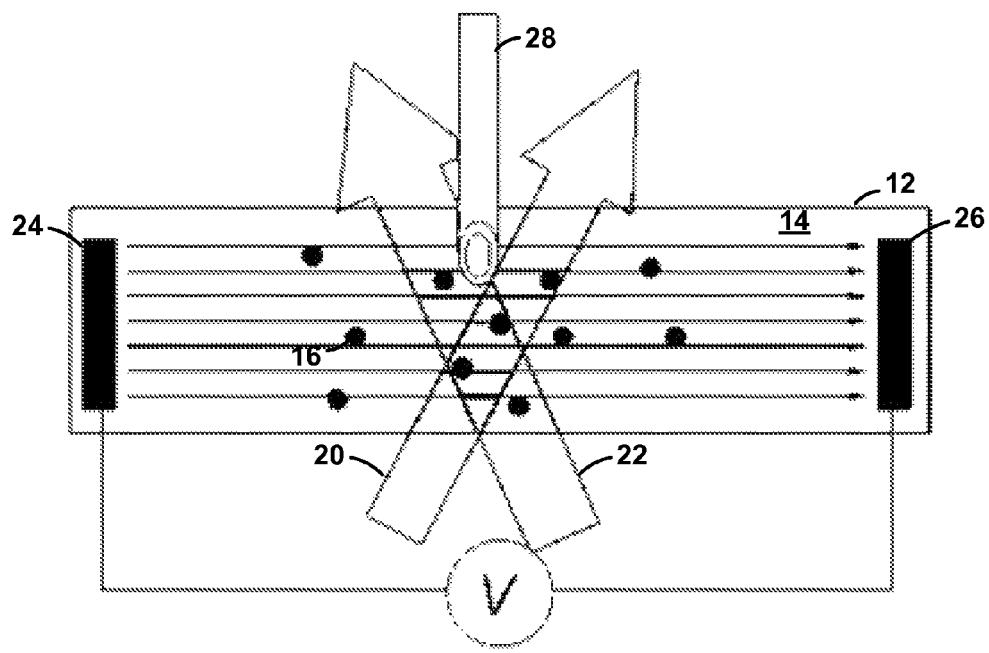
FIG. 2D is a schematic diagram illustrating the electrophoretic apparatus shown in FIG. 2A after a third time period has elapsed and the electrophoretic measurement is complete.

Referring to FIG. 2A, an illustrative electrophoretic apparatus according to one aspect of the invention includes a cell 12 with an introduction channel 28, such as a needle. The introduction channel allows a user to introduce a sample, such as a protein sample into a buffer/dispersant 14 at a location that is separated from the electrodes.

Referring to FIGS. 2A-2D, in operation, the sample cell is filled, initially, only with the buffer in which the sample itself is dispersed in and not the sample itself (see FIG. 2A). The sample is added only to a small region in the vicinity of the detection volume and the measurement started. The measurement proceeds for long enough to record an accurate estimate of the electrophoretic mobility (see FIGS. 2B-2D), but not long enough for the sample to have reached the electrodes. This means that the sample may be retrieved, albeit diluted, afterward without the presence of electrode aggregates.

Figure 3:
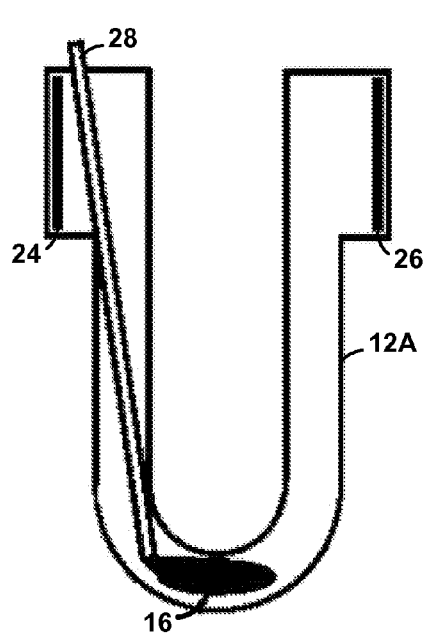
FIG. 3 is a schematic diagram of a u-shaped electrophoretic apparatus according to the invention.

Referring to FIG. 3, the electrophoretic apparatus can be based on an upright u-shaped cell 12A in which a sample 16 is injected in an optical detection region at the base of the cell. This provides a relatively long channel length for a given footprint to hold the buffer that acts as a diffusion barrier. The diffusion barrier is intended to isolate the sample (protein, soft sample or otherwise) from the electrode surface whilst maintaining electrical contact with the surface, via the buffer within which the sample is dispersed, for an electrophoretic measurement. In another embodiment, conductive gel plugs, such as agar, which can hinder diffusion further, could be added to the folded cell channel.

Figure 4:
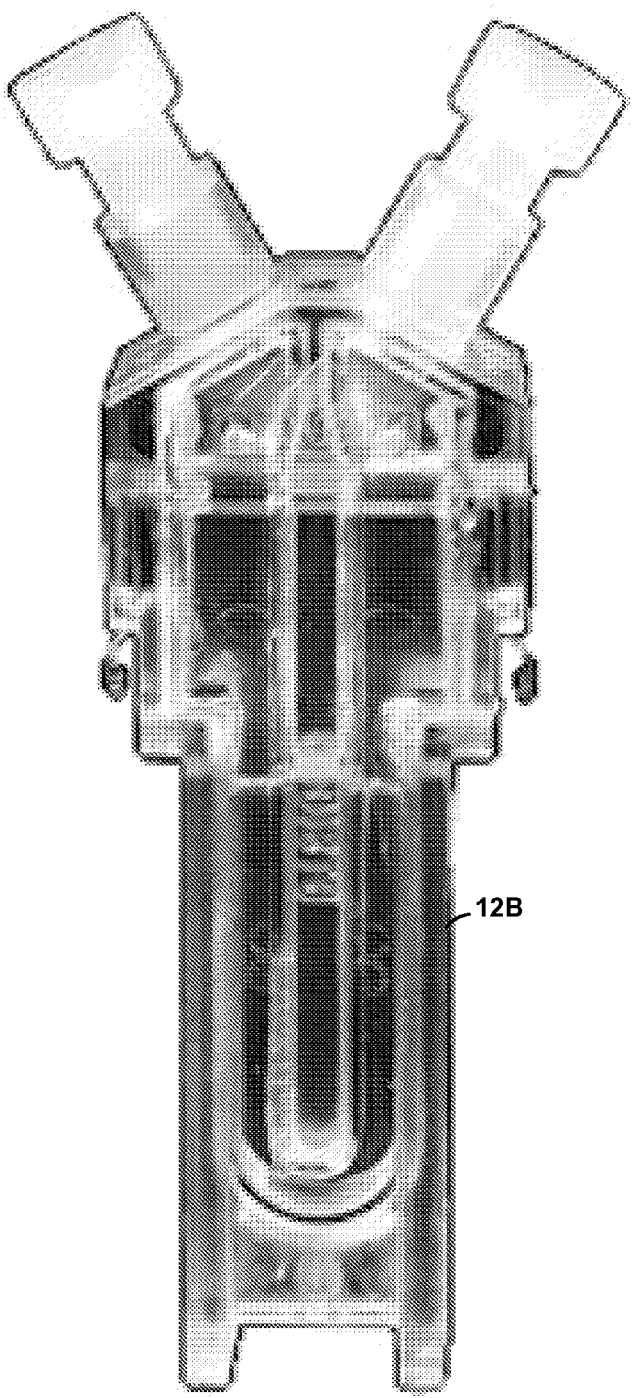
FIG. 4 is a photographic illustration of an implementation of the u-shaped electrophoretic apparatus of FIG. 3.

Referring to FIG. 4, the u-shaped electrophoretic apparatus can be implemented as a plastic cell that is compatible with an existing light scattering measurement system, the Zetasizer Nano, which is available from Malvern Instruments Ltd of Malvern, UK, and is described in PCT published application WO2010041082 entitled APPARATUS FOR HIGH-THROUGHPUT SUSPENSION MEASUREMENTS, which is herein incorporated by reference. The Zetasizer Nano can perform different types of measurements, but laser Doppler electrophoretic measurements are the most sensitive for mobility measurements.

In laser Doppler electrophoretic measurements, the velocity of particles is measured using the technique of laser Doppler anemometry. The frequency shift or phase shift of an incident laser beam caused by the moving particles is measured as the particle mobility, and this mobility can then be converted to a zeta potential of the particles by inputting the dispersant viscosity, and the application of the Smoluchowski or Huckel theories. These theories are approximations useful for most applications. More recent models are available which can give a more exact conversion, but require more knowledge of the chemistry of the dispersion.

Figure 5:
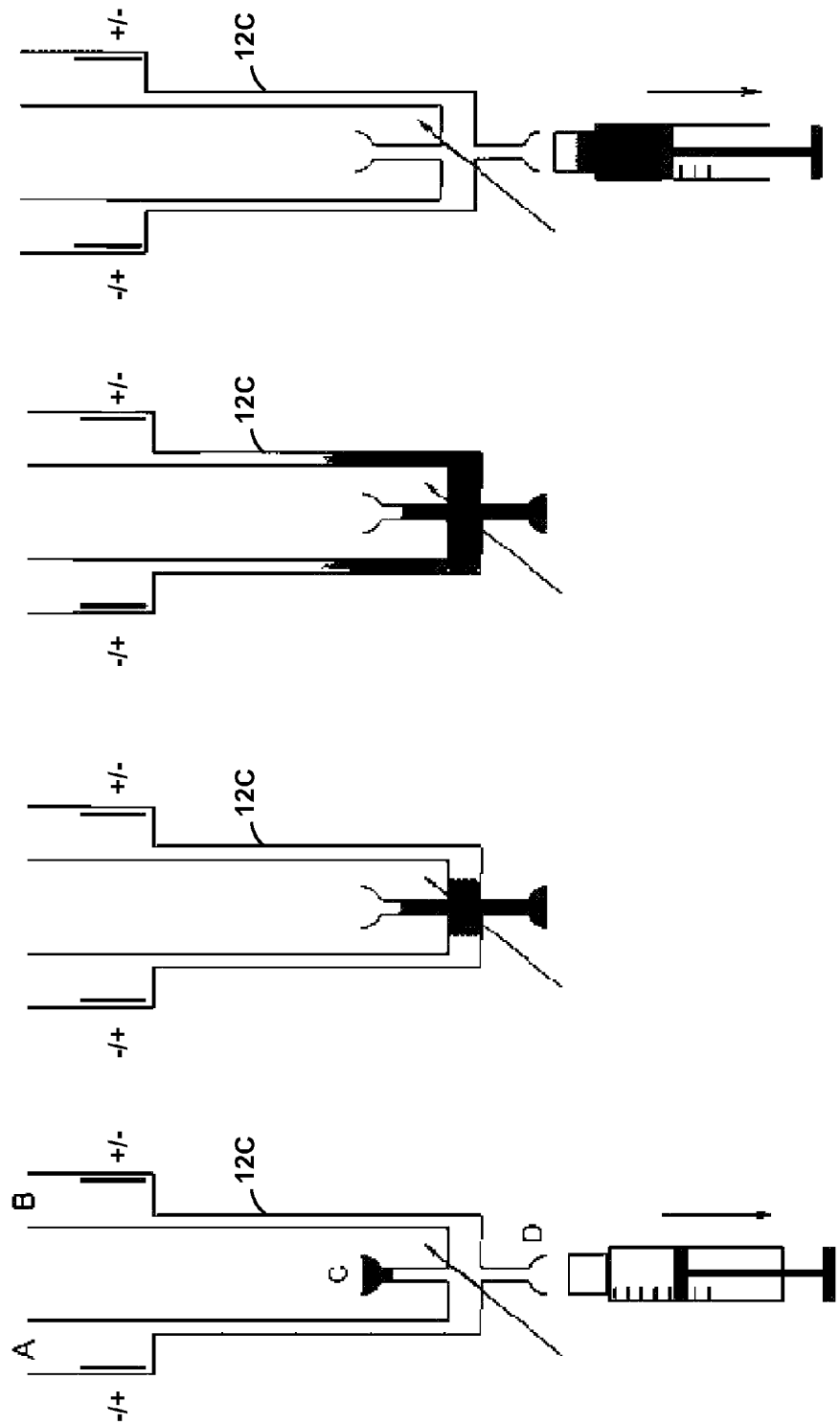
FIG. 5A is schematic diagram of a u-shaped electrophoretic apparatus according to the invention that is equipped with introduction and extraction channels, shown before instruction of a sample.
FIG. 5B is schematic diagram of the electrophoretic apparatus of FIG. 5A shown during introduction of the sample.
FIG. 5C is schematic diagram of the electrophoretic apparatus of FIG. 5A shown after an electrophoretic mobility measurement for the sample.
FIG. 5D is schematic diagram of the electrophoretic apparatus of FIG. 5A shown after extraction of the sample for which the mobility measurement was performed.

Referring to FIG. 5, a multi-port folded capillary cell 12C can also be used to perform electrophoretic measurements according to the invention. The basic concept is outlined in FIGS. 5A-5D. The cell consist of four ports, two for diluent only (A and B), and two for sample only (C and D). A three-port version would combine the functionality of ports C and D.

Figure 6:
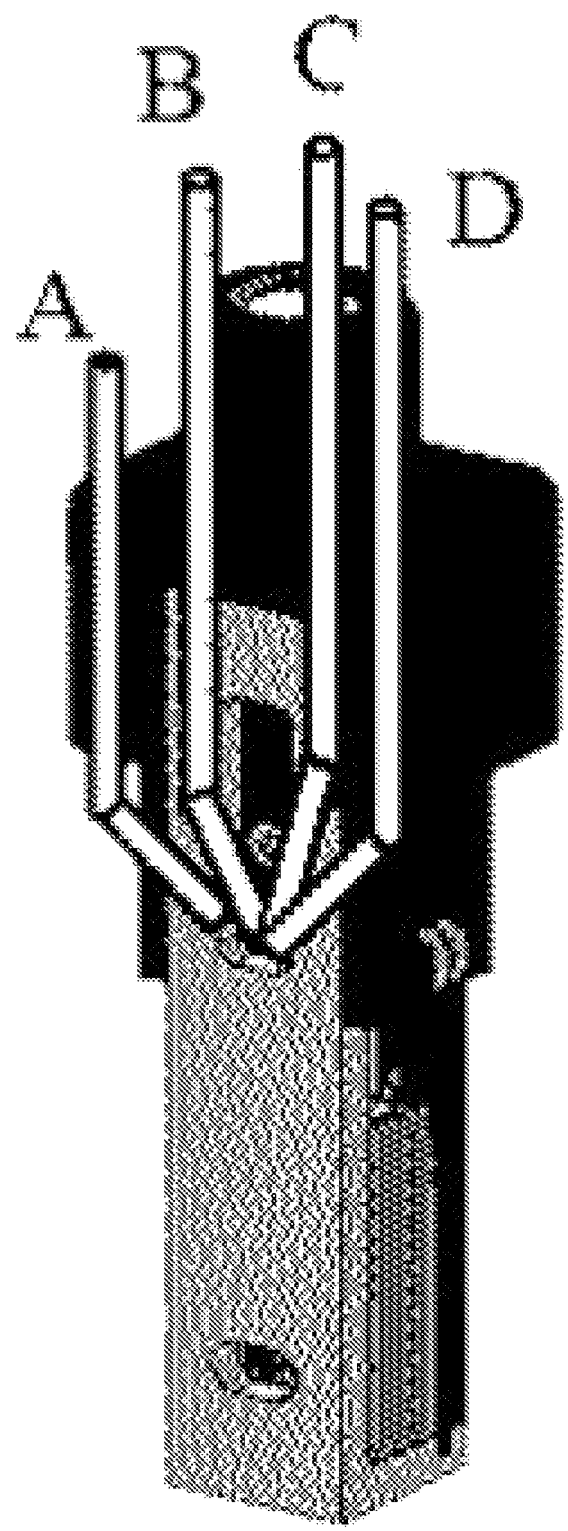
FIG. 6 is a schematic diagram of an embodiment of the electrophoretic apparatus of FIG. 5A.

In operation, the whole cell 12C is filled with the buffer within which the sample is dispersed (FIG. 5A). The sample is dropped (pippetted) into the sample cup C and the syringe draws the sample into the measurement chamber (FIG. 5B). The LDE measurement is started immediately. Once the measurement is complete (FIG. 5C), the sample will have diffused someway along the cell arms. Fast field measurements are not affected by electro-osmotic 'sloshing' of the sample from electrode chamber to electrode chamber so these chambers are left open at their top and the cell is swept clean by the syringe retrieving the sample, albeit in diluted form (FIG. 5D). Referring to FIG. 6, the multiport cell can also be engineered into a convenient folded form for the Zetasizer Nano.

Figure 7:
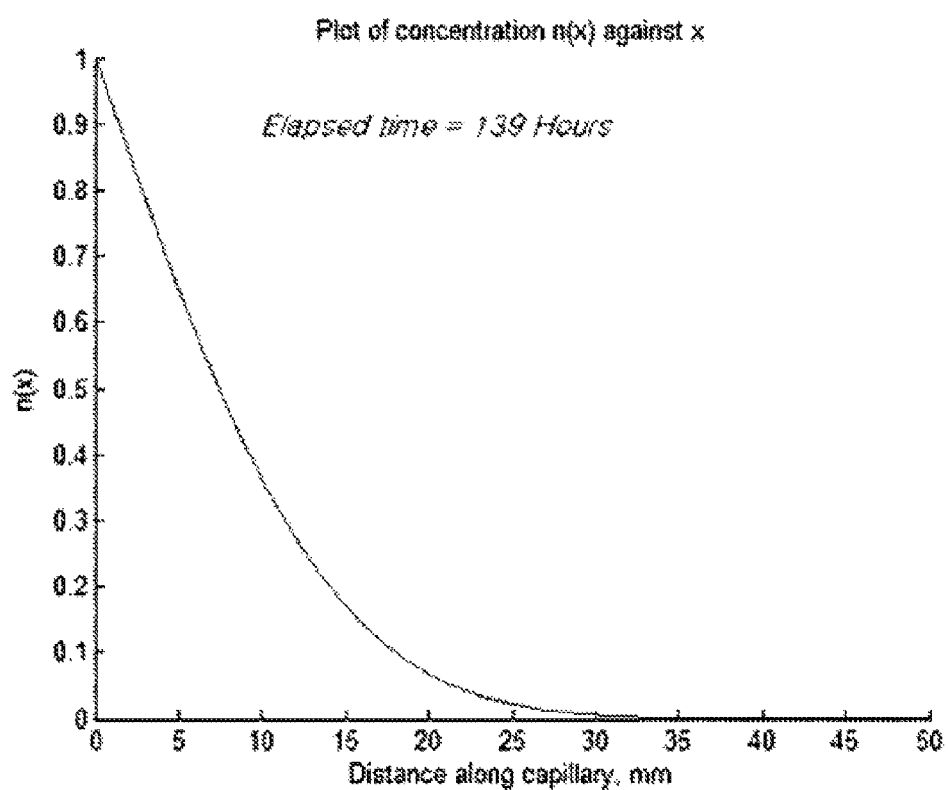
FIG. 7 is a plot of concentration against distance for an electrophoretic apparatus according to the invention.

Referring to FIG. 7, the diffusion barrier required for a particular measurement can be determined using Fick's first law. Fick's first law describes the concentration, n, at time, t, at a distance x, from a constant concentration source, n(0) and is given by $$n(x, t) = n(0) \operatorname{erfc}\left(\frac{x}{2\sqrt{Dt}}\right) \quad (1)$$

where erfc( ) is the complementary error function. D is the diffusion co-efficient. We focus on lysozyme here with $D=120$ μm2/s measured using a Zetasizer Nano ZS.

FIG. 7 shows that many hours need to have elapsed before a lysozyme sample has significantly diffused a distance of 30 mm from the source at x=0. The times taken for protein mobility measurements using micro-electrophoresis are on the order of a few minutes to a few tens of minutes. These are much smaller timescales than shown in FIG. 7. It is likely that convection currents and residual electroosmosis would reduce the times shown in FIG. 7 significantly but it is adequate as a limiting estimate to highlight the theoretical basis for the technique. That is, that LDE measurements can be performed within the time taken for the protein to migrate to the electrode surface if it is required that the sample is retrieved. Or in the time taken for the protein to reach the electrodes plus the time taken for the subsequent protein/ electrode aggregates to migrate back from the electrodes to the detection area when it is not required that the protein sample be retrieved intact.

The present invention has now been described in connection with a number of specific embodiments thereof. However, numerous modifications which are contemplated as falling within the scope of the present invention should now be apparent to those skilled in the art. For example, other cell geometries and injection and/or extraction mechanisms could be devised, and the method could be applied to other types of samples. Therefore, it is intended that the scope of the present invention be limited only by the scope of the claims appended hereto. In addition, the order of presentation of the claims should not be construed to limit the scope of any particular term in the claims.

What is claimed is:

1. An electrophoretic measurement method, comprising:
   providing an upright u-shaped vessel that holds a dispersant,
   providing a first electrode immersed in the dispersant,
   providing a second electrode immersed in the dispersant,
   placing a sample at a location within the dispersant between the first and second electrodes with the sample being separated from the electrodes,
   applying an alternating electric field across the electrodes,
   illuminating the sample with temporally coherent light,
   detecting a frequency shift in light from the step of illuminating that has interacted with the sample during the step of applying an alternating electric field, and
   deriving a property of the sample based on results of the step of detecting.

2. The method of claim 1 wherein the step of placing the sample includes injecting the sample.

3. The method of claim 1 wherein the step of placing the sample is part of a process of drawing the sample through the vessel.

4. The method of claim 1 further including a step of recovering the sample.

5. The method of claim 1 wherein the sample is a soft sample.

6. The method of claim 1 wherein the sample is a protein sample.

7. The method of claim 1 wherein the step of placing the sample places the sample at a location separated from the electrodes by dispersant.

8. The method of claim 1 wherein the step of placing the sample places the sample at a location separated from the electrodes by a barrier different from the dispersant.

9. The method of claim 1 wherein the step of deriving includes deriving a zeta potential value from an electrophoretic mobility value for the sample.

10. The method of claim 1 wherein the step of detecting takes place in a time that is shorter than a time during which a significant amount of the sample can diffuse to either of the first and second electrodes with the alternating current applied.

11. The method of claim 1 wherein the step of illuminating employs a laser.

12. The method of claim 1 further including a step of recovering the sample before the sample has fully diffused into the dispersant.

13. The method of claim 1 wherein the step of placing includes placing the sample around the bottom of the u-shaped vessel.

* * * * *